(12) United States Patent
Lamb

(10) Patent No.: US 6,609,518 B2
(45) Date of Patent: Aug. 26, 2003

(54) BREATHING AID DEVICE

(75) Inventor: Derek Lamb, Keighley (GB)

(73) Assignee: Viamed Ltd. (GB)

( * ) Notice: Subject to any disclaimer, the term of this patent is extended or adjusted under 35 U.S.C. 154(b) by 0 days.

(21) Appl. No.: 09/682,464

(22) Filed: Sep. 6, 2001

(65) Prior Publication Data

US 2002/0046753 A1 Apr. 25, 2002

(30) Foreign Application Priority Data

Sep. 9, 2000 (GB) ............................................. 0022285

(51) Int. Cl.[7] ........................... A61M 16/00; A62B 7/00; A62B 9/00
(52) U.S. Cl. ......................... 128/204.25; 128/204.18; 128/204.24; 128/205.11; 128/205.24; 128/206.24
(58) Field of Search ................... 128/204.18, 204.25, 128/205.11, 205.24, 204.22, 204.23, 204.24, 911, 200.24, 206.24, 206.26, 205.19

(56) References Cited

U.S. PATENT DOCUMENTS

| | | | | |
|---|---|---|---|---|
| 3,717,147 A | * | 2/1973 | Flynn | 128/204.25 |
| 3,769,973 A | * | 11/1973 | Esbenshade, Jr. | 128/200.14 |
| 4,297,999 A | * | 11/1981 | Kitrell | 128/205.16 |
| 4,898,167 A | * | 2/1990 | Pierce et al. | 128/205.11 |
| 5,186,166 A | * | 2/1993 | Riggs et al. | 128/203.15 |
| 5,542,416 A | * | 8/1996 | Chalvignac | 128/204.23 |
| 5,655,520 A | * | 8/1997 | Howe et al. | 128/203.12 |
| 5,664,562 A | * | 9/1997 | Bourdon | 128/204.18 |
| 5,678,541 A | * | 10/1997 | Garraffa | 128/204.26 |
| 5,724,963 A | * | 3/1998 | Seeley | 128/205.24 |
| 5,931,159 A | * | 8/1999 | Suzuki et al. | 128/204.18 |
| 6,029,660 A | * | 2/2000 | Calluaud et al. | 128/200.21 |
| 6,135,108 A | * | 10/2000 | Hoenig | 128/204.18 |
| 6,279,574 B1 | * | 8/2001 | Richardson et al. | 128/204.17 |
| 6,443,154 B1 | * | 9/2002 | Jalde et al. | 128/201.28 |

* cited by examiner

Primary Examiner—Weilun Lo
Assistant Examiner—Michael Mendoza
(74) Attorney, Agent, or Firm—Ronald E. Smith; Smith & Hopen, P.A.

(57) ABSTRACT

An intermittent positive pressure breathing device for neonatal infants. The device is connected to a supply of pressurized oxygen supplied through a first conduit. The first conduit terminates in a venturi nozzle by which ambient air is entrained so that a mixture of oxygen and ambient air at a desired concentration is delivered along a second conduit towards the mouth of the neonate. The second conduit terminates in a mask having a first aperture disposed adjacent the mouth of the neonate in a sealing relationship and a second aperture which is repeatedly and rhythmically covered by the operator to initiate a conventional breathing pattern for the neonate. A one way valve upstream of the venturi nozzle opens when the venturi nozzle induces a lower than atmospheric pressure in the device and automatically closes when the pressure in the device is increased by the operator closing off the second aperture.

8 Claims, 6 Drawing Sheets

BREATHING AID DEVICE

BACKGROUND OF INVENTION

This invention relates to a device for aiding breathing and particularly for aiding the initiation of regular breathing in neonates, although the following description is in no way limited to this specific application. Those skilled in the art will immediately understand from the following description that the invention may be used as a breathing, inspiration or inhalation aid for any class of mammal, whether human or animal. In the interests of clarity and as the invention is most applicable to the initiation of breathing in neonates, the invention will now be described with reference to this particular application.

Neonates often encounter breathing difficulties in the first few minutes following birth. During gestation, the lungs of the fetus are fluid filled and relatively compressed, with gas exchange occurring across the placenta. Oxygen diffuses across the placenta moving from the mother's blood to the fetus's blood and carbon dioxide moving in the reverse direction. At birth, the placenta is cut and the neonate has to initiate breathing independently of the mother to allow the continuation of gas exchange, thus ensuring the neonates survival. The neonate expands its lungs with air, thereby allowing gas exchange to take place between the pulmonary alveoli and the pulmonary capillaries. The neonate often encounters difficulties with the initial expansion of the lungs, thereby resulting in neonatal breathing problems.

Breathing apparatus is typically used on the neonate until regular breathing is initiated. Conventionally, this breathing apparatus has consisted of a facemask supplied with oxygen that is placed over the neonate's mouth. An expandable bag is attached to the facemask and an operator of the apparatus has to manually compress the bag repeatedly to ensure the correct pressure of oxygen reaches the neonate's lungs to aid the expansion of the same. This process can sometimes be required for up to 20 minutes and can become very tiring for the operator and resulting in uneven compression of the bag and thus non-uniform forced breathing of the neonate.

A modified version of the bag expansion apparatus is now used and has been designed to reduce the effort required by the operator to pump air into the neonate's lungs. An example of such a device is manufactured under the trademark Tom Thumb® and comprises a pressurized pure oxygen source connected to a flow meter, which in turn is connected to a pressure release valve and then to a facemask, which is placed over a neonate's mouth. The facemask is provided with an aperture at its rear on the alternate side to that which comes into contact with the neonate proximate its mouth, which an operator of the device Intermittently covers and uncovers, usually with a thumb, to ensure that the pressured gas enters the lungs as opposed to escaping through the aperture. Immediately on applying a thumb over the aperture, there is a pressure build up in the pipe that connects the mask and the pressure release valve. Said pressure release valve can be adjusted to regulate the pressure at which the pure oxygen (which is typically the only piped gas in modem hospitals, although some are now being provided with piped air) is supplied to the neonate's lungs and thus in normal operating circumstances when a thumb is placed over the aperture, the pressure build up within the tube is sufficient to cause the pressure valve to release and the majority of the oxygen is expelled therethrough. The remainder of the oxygen enters the neonate's lungs at the desired pressure.

This device is found to be effective in initiating neonatal breathing.

Research and customer feedback, particularly from hospitals in the western world where the device is most commonly used, has shown that a mixture of air and oxygen is preferable to pure oxygen for inhalation by the neonate. A device such as described has been proposed which uses an oxygen-air mix by connecting both piped oxygen and piped air to a mixing block wherein the volumes of the pure oxygen and air mixed can be adjusted to give an output gas stream of a desired oxygen concentration. This arrangement obviously necessitates a supply of both pure oxygen and air. Two flow meters may be provided to monitor and control the pressure from each gas source and to ensure adequate diffusion of the same. The disadvantage of such apparatus is that the use of two flow meters is prohibitively expensive. In addition, although bottled and/or piped oxygen is usually available in most hospital and medical practices, bottled and or piped air is frequently not available. For example, bottled air is rarely supplied in the hospitals and medical practices of third world countries, in emergency situations, in midwifery, for home visits or the like.

There are additionally known intermittent positive pressure breathing devices, more commonly referred to as IPPB devices. IPPBs are simple mechanical respiratory ventilators which are primarily designed for home use by elderly or infirm patients who have difficulty breathing unassisted but are sufficiently mentally capable of operating the device.

Ohio Medical Products Inc., a division of Airco Inc., has in the past published product leaflets describing two different types of IPPB identified by the trademark HAND-B-VENT both of which function to deliver a pressurized stream of an oxygen/air mixture to the patient when a normally open aperture of the device is manually closed by said patient. The first of these devices, shown schematically in FIG. 1, includes a source of pressurized oxygen 10 which is delivered along a conduit 12 past a needle valve 14 and a pressure measuring device 16 and is ultimately forced through a venturi jet 18 in a second conduit 20. The first open end 22 of conduit 20 is disposed adjacent the mouth of the patient and the pressurized gas is thus forced into the patient's lungs. Within conduit 12 is provided a connection at 24 by which a nebulizer 26 is connected into the system, said nebulizer being used where it is additionally desired to provide a medical or therapeutic aerosol to the patient. Also within conduit 12 is provided a manually operable closing control 28, which in its simplest embodiment is operated by the patient closing the control by placing a thumb over the open port. Gas flowing through the venturi mixes with the gas and medicated particles from the nebulizer.

Upstream of the venturi nozzle 18 in conduit 20 are provided firstly an exhalation valve 30 and an inhalation flow control device 32.

In use the patient places the open end 22 against his mouth and closes the control 28 during inspiration only, which in turn forces oxygen through the venturi. Ambient air present in conduit 20 is entrained through the venturi upstream thereof and delivered to the patient at a desired pressure determined by the particular setting of the needle valve 14. It is to be noted that in this device, air is continuously entrained when the control 28 is closed. After the patient has inspired to a sufficient degree, the control 28 is opened, the pressurized oxygen exhausts through the now open control, and the exhalation gas of the patient passes in opposite direction along conduit 20 from that of the gas during inhalation, past the venturi and towards the exhalation valve 30. Since the venturi entrains gas through the conduit 20, the total gas flow rate to the patient can be controlled by adjusting the flow rate control valve 32. In order that the patient may exhale against zero resistance, a one-way gas exhalation valve 30 must be used with the flow rate control 32. Gas cannot be entrained through the exhalation valve during inspiration, but only along conduit 20 past the flow control valve 32.

An alternative configuration of venturi IPPB device is schematically shown in FIG. 2 which includes a source of pressurized air (typically provided by a rotary compressor 40) delivered along a conduit 42 to which is connected a second conduit 44 in which is provided a needle valve 46 which controls the amount of gas which is allowed to bleed out of the system—the more gas that is allowed to bleed out the system, the less the pressure of the gas delivered to the patient, and vice versa.

A pressure-measuring device 48 is provided and the conduit 42 is connected to a nebulizer 50 having a nozzle 52 and an air entrainment aperture 54. A venturi constriction is provided at 55. The function of the nebulizer in this device is twofold: firstly to produce a mist and secondly to entrain gas through the venturi through entrainment aperture 54.

A manually operable closing control 56 is provided in the low pressure part of the system, in particular in conduit 58 which has an open end 60 which is placed adjacent a patient's mouth and from which a pressurized gas stream emerges. In use when the patient wishes to inspire, a thumb is placed over control 56 to close same (in much the same manner as the aperture of the face mask placed adjacent a neonate's mouth is closed as described above). Control 56 has two functions in this embodiment because when open, the control functions simply as an exhalation port through which gas exhaled by the patient passes. When control 56 is closed, this port is shut off and pressurized gas stream is prevented from merely exhausting through control 56. Again, in this system gas is entrained continuously irrespective of whether the control 56 is closed or open, and thus whether the patient is inspirating or expirating.

The reader is referred to Canadian Patent No. 901 915 issued in 1972 for a more complete description of an IPPB device.

The disadvantages of the systems described is manifold. Firstly, these IPPB devices are designed to deliver a medicated aerosol or nebulized mist to the patient on each inspiration. The successful operation of both devices, and indeed all venturi-based devices is a cooperative patient who is mentally and physically able to operate the manual system closing control rhythmically with his respiratory cycle. These devices are therefore wholly inappropriate for initiating the breathing of neonates.

Secondly, there is no facility for adjusting the quantity of air entrained during operation and thus the oxygen concentration of the gas delivered to the patient cannot be altered. Thirdly, there is no pressure release within either of these systems, so it is possible that patients could over inflate their own lungs with obvious detrimental consequences, especially where medicated aerosols are being delivered.

Finally, there is no means of delivering a predetermined volume of breathable gas having a desired oxygen concentration to a patient because the devices described operate to deliver a continuous breathable gas stream of fixed oxygen concentration to a patient.

It is therefore an object of the present invention to provide an inexpensive breathing aid device which is capable of supplying a mixture of air and oxygen with a desired oxygen concentration to a patient.

SUMMARY OF INVENTION

According to the present invention there is provided a device suitable for aiding, forcing or initiating the breathing of living beings, said device comprising a venturi device within a first conduit means by which air can be entrained through said first conduit means from behind said venturi device, a second conduit means of predetermined length provided in front of said venturi device, said second conduit means being of a significantly greater diameter than the smallest diameter of the venturi device so as not to adversely affect the entrainment of air thereby, said second conduit means being coupled to mask means having a first and second apertures through which gas can exhaust, said first aperture being ideally disposed in sealing relationship with an air intake passage of a living being, characterized in that a pressure actuable valve having open and closed conditions is provided in the first conduit means upstream of said venturi with entrained air necessarily passing through said valve when open, said valve being automatically closed when the second aperture of the mask means is blocked thus immediately increasing the pressure in the first and second conduit means and constraining the volume of gas within the second conduit means to be pressuredly delivered to the living being through the first aperture of said mask means.

Preferably, pressure release means is provided downstream of said venturi device in said second conduit means to allow for venting of gas therethrough when the pressure within said second conduit means exceeds a predetermined threshold. Preferably the pressure release means is adjustable in that the threshold pressure can be set as desired.

Preferably the device is coupled to a source of substantially pure oxygen.

Preferably the length of the second conduit means and the threshold pressure of the pressure release means is determined according to the capacity of the lungs of the living being.

Preferably the extent of the opening of the pressure actuated valve when in its open condition can be adjusted so that the volumetric quantity of entrained air, and thus the ultimate concentration of oxygen in the gas within the second conduit means can be selectively altered when the second aperture of the mask means is open and air is being entrained.

The pressure release means can be any conventional pressure release valve. For example, a blow off valve can be used which releases gas from the second conduit means when the pressure therein reaches a certain threshold value.

The disposition of the venturi between the pressure release valve and the pressurized gas inlet is of advantage for the following reason. When an operator sealingly closes off the second aperture in the mask, and thus prevents exhaust of the gaseous mixture therethrough to atmosphere, a step increase in the pressure in the first and second conduit means results on account of the resistance of the lungs of the living being to expansion. This step pressure increase travels back up the tubing almost instantaneously to the pressure actuated valve which is immediately closed, and the gaseous mixture within the second conduit means is then delivered through the first aperture in the mask to the living being. As the lungs of said living being are expanded to capacity, the pressure in first and second conduit means increases above the threshold pressure level of the pressure release means, and thus excess gas (which is now pure oxygen, as no air is being entrained during delivery to the living being) is exhausted to atmosphere through said release.

There is a further advantage of the device of the invention as compared to the devices of the prior art. In this device, the second aperture in the mask allows expirated gases to flow immediately therethrough without needing to travel along any part of the second conduit. Hence, this arrangement ensures that the subsequent delivery of gas to the human is in no way polluted with expirated gases.

Preferably the second aperture in the mask is structured such that an operator of the device can cover and uncover said second aperture with a finger or other blocking means, thereby periodically releasing gas from the device.

The breathing aid device has the advantage that it does not require a power source or bottled air and can be driven by the pressure from the pressurized oxygen source. The device is therefore more easily transportable than when two pressured gas supplies are required. A further advantage is that venturi is inexpensive and thus preferable to other expensive alternatives.

Most preferably the venturi is adjustable so that the amount of ambient air entrained can be adjusted.

BRIEF DESCRIPTION OF DRAWINGS

An embodiment of the present invention will now be described with reference to the following figure wherein.

DETAILED DESCRIPTION

Figure 1:
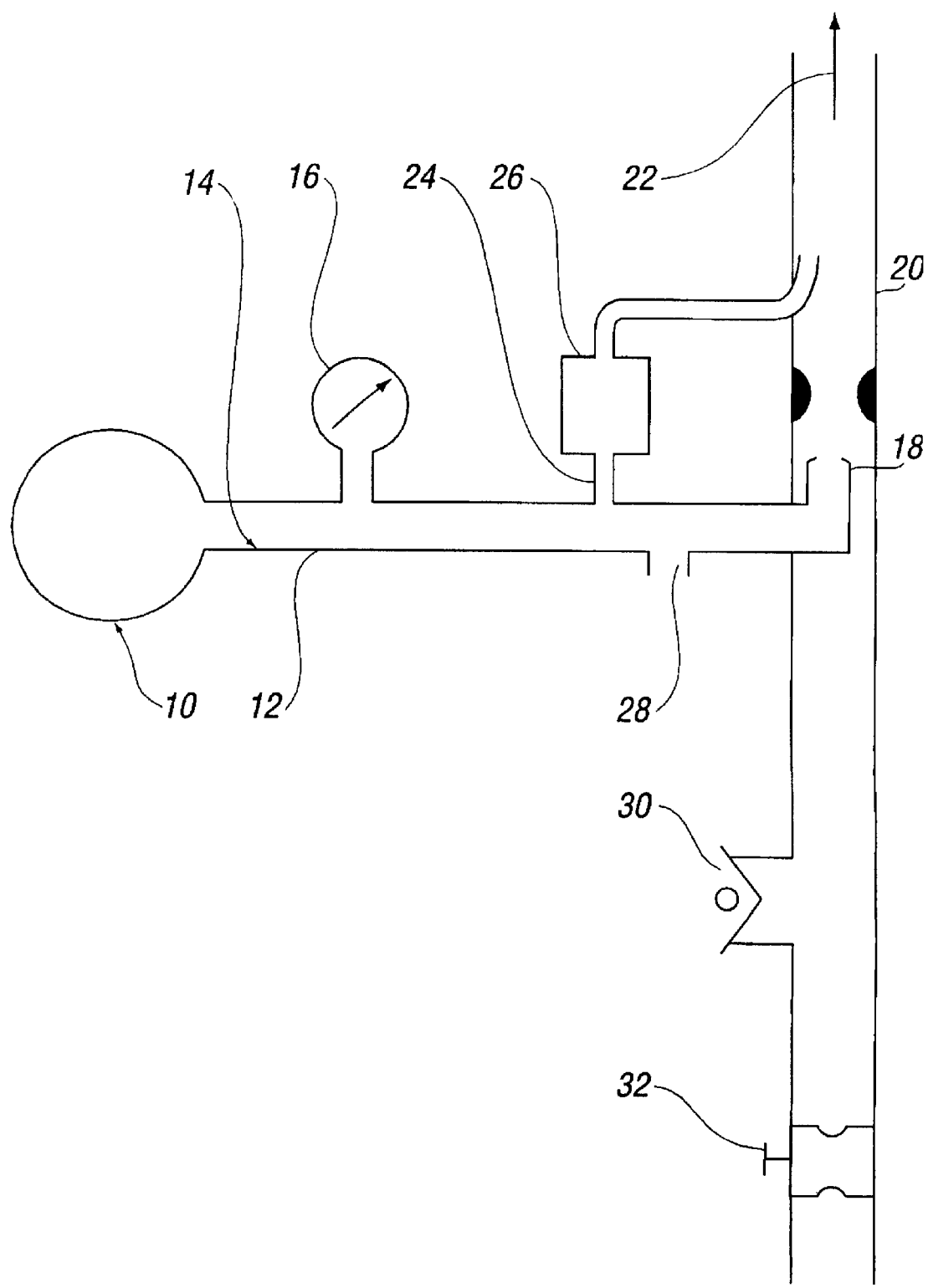
FIGS. 1 and 2 schematically show devices of prior art configuration.
Figure 2:
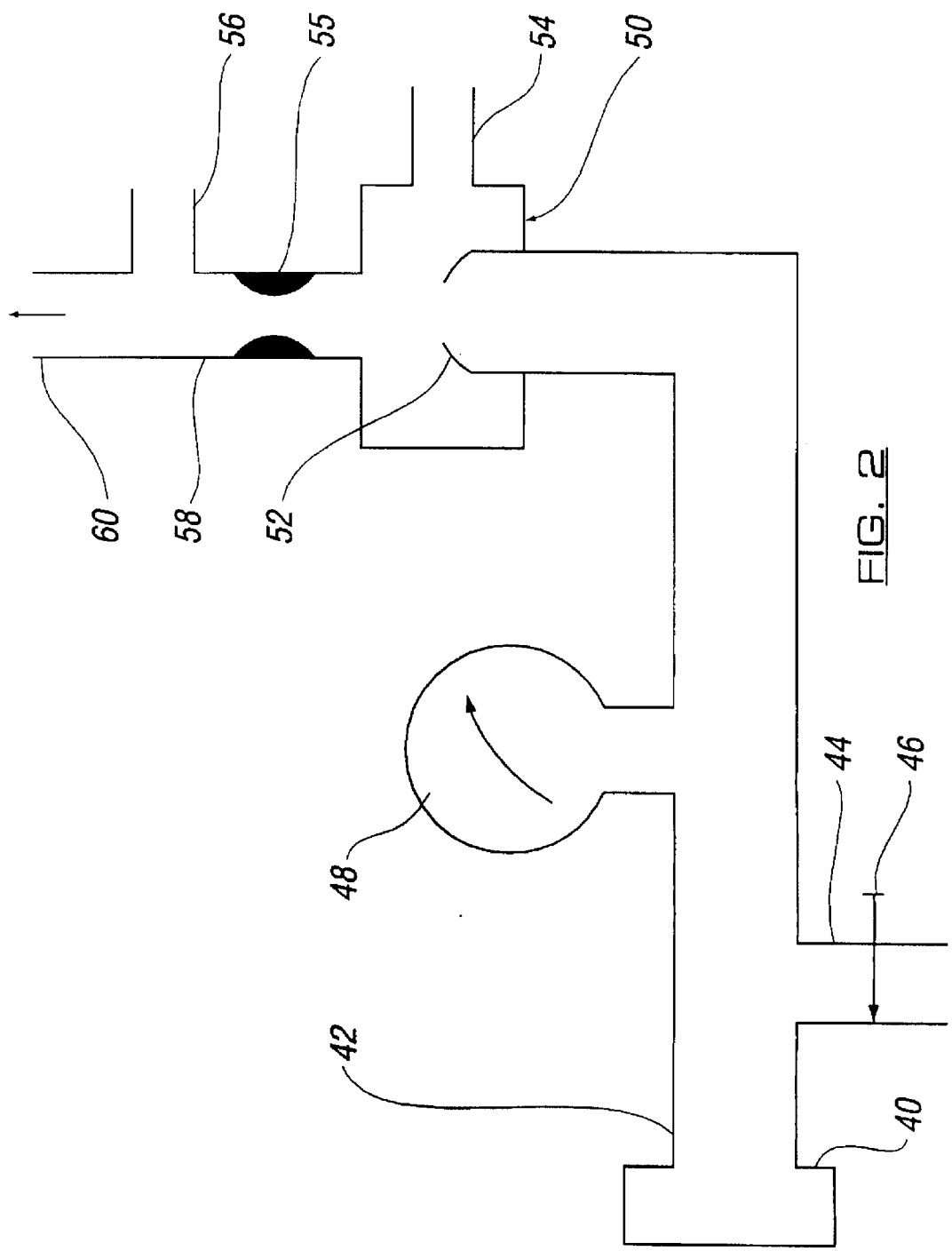
Figure 3:
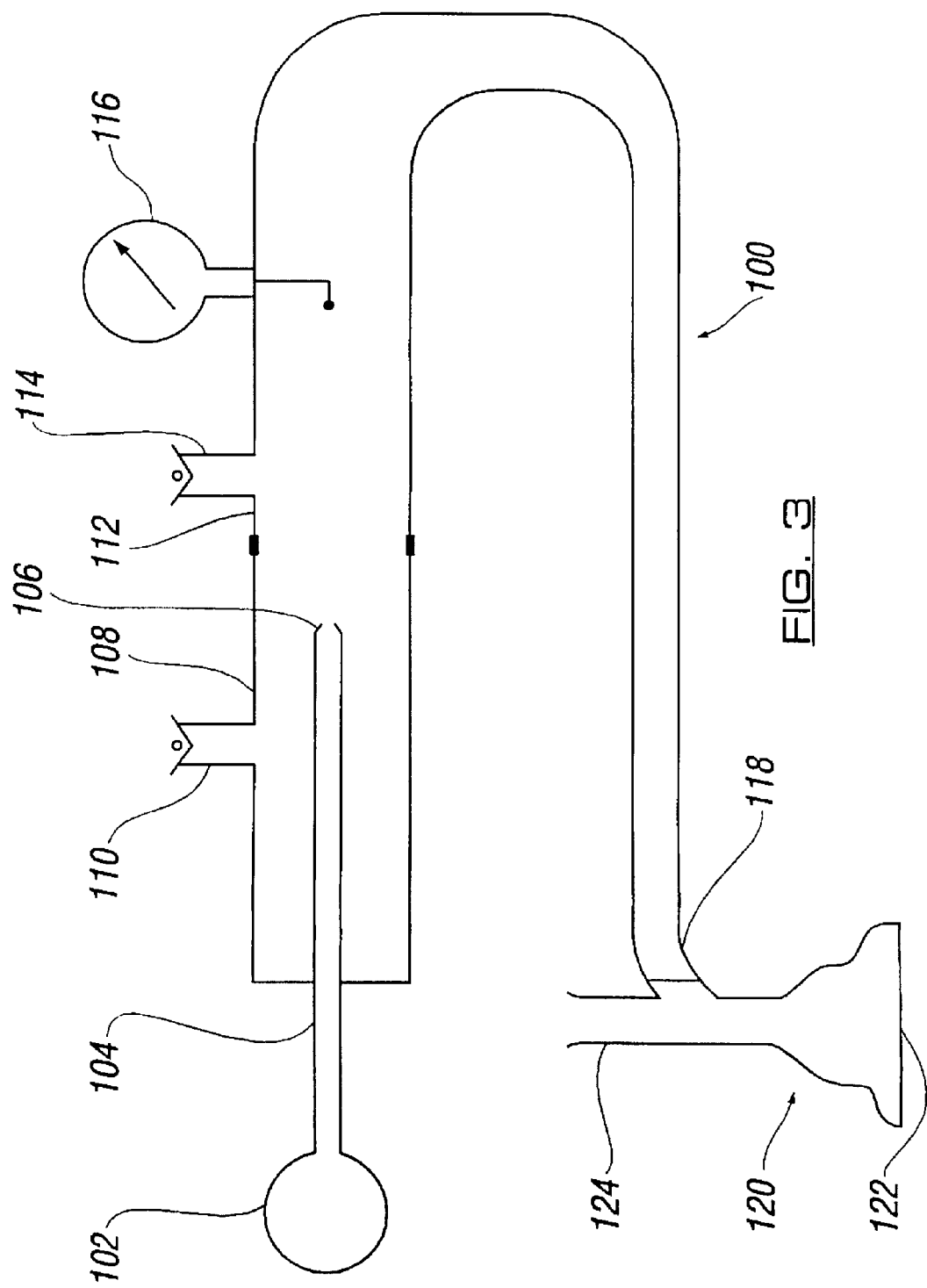
FIG. 3 shows a schematic representation of a device according to the invention.

Referring to FIG. 3, there is shown a schematic representation of apparatus 100 for assisting the inspiration of a living being. The apparatus is connected to a pressurized supply 102 of oxygen which is fed through tubing 104 to a venturi nozzle 106 provided within a first conduit 108. Upstream of said venturi nozzle and within the first conduit 108 is provided a one-way pressure actuated valve 110 through which air can be entrained when the pressure within conduit 108 is at or below ambient pressure. The first conduit is connected to a second conduit 112 in to which are connected a pressure release valve 114 and an oxygen concentration monitor 116. Said second conduit is of a predetermined or calculated length so that the volume of gas within said second conduit is sufficient to inflate the lungs of a living being to a suitable extent with oxygen enriched breathable air. At a remote end 118 of said second conduit there is connected a T-occluder 120 consisting of a mask portion 122 and an outlet 124 on the opposite side of said T-occluder which is of a size capable of being blocked by the thumb or finger of an operator.

Figure 4:
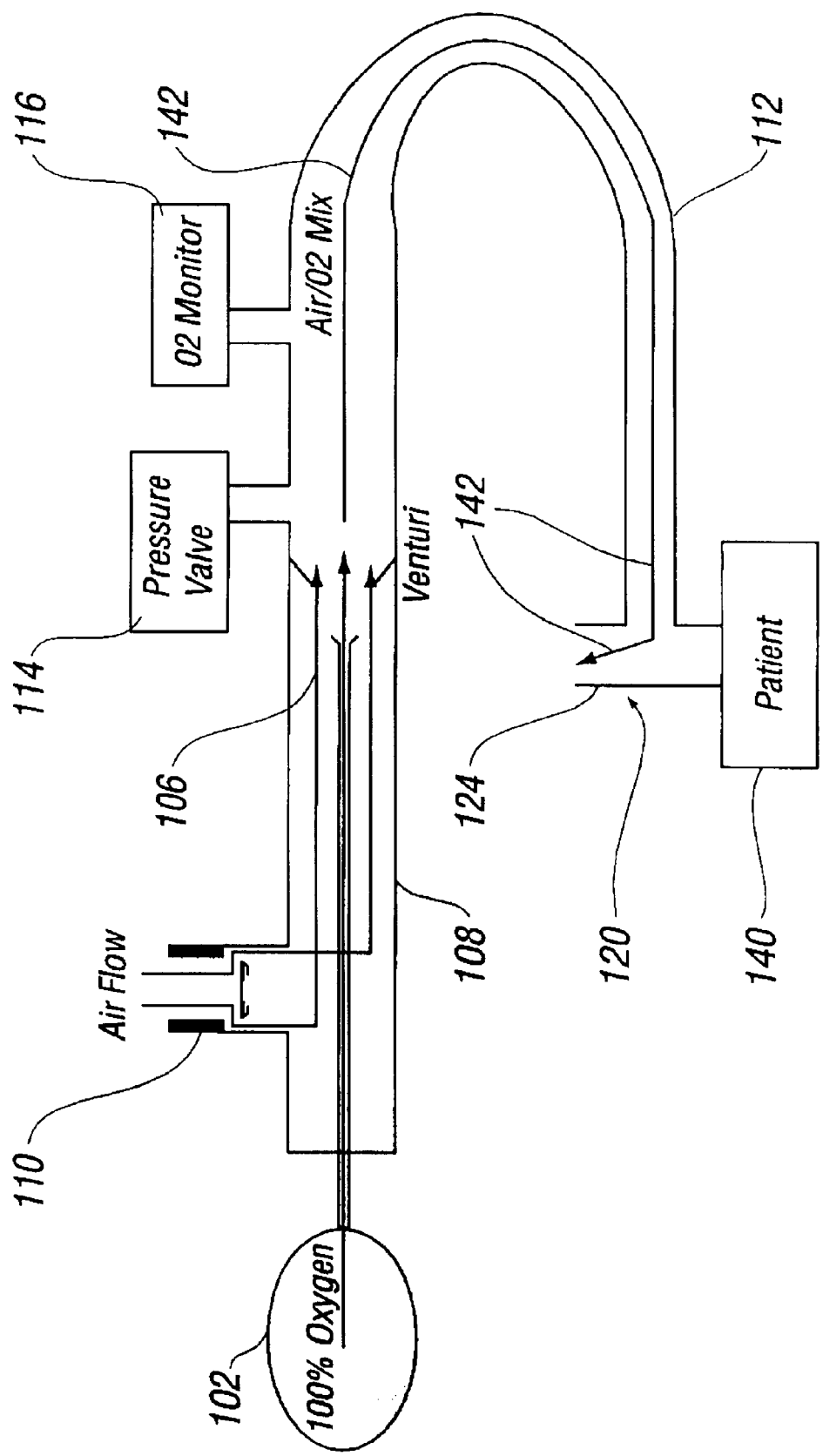
FIGS. 4, 5 and 6 show schematically how the device according to the invention functions.
Figure 5:
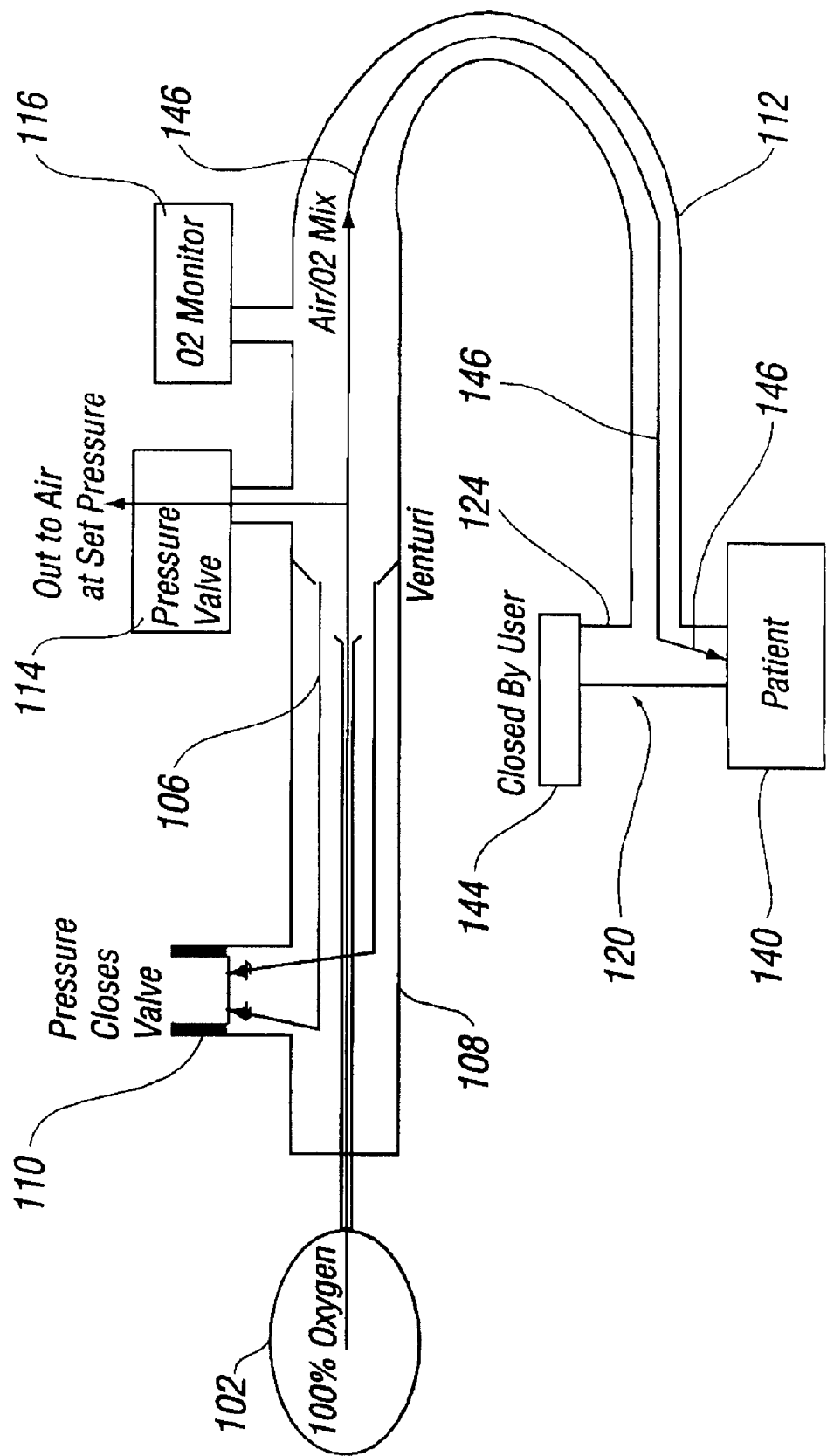
Figure 6:
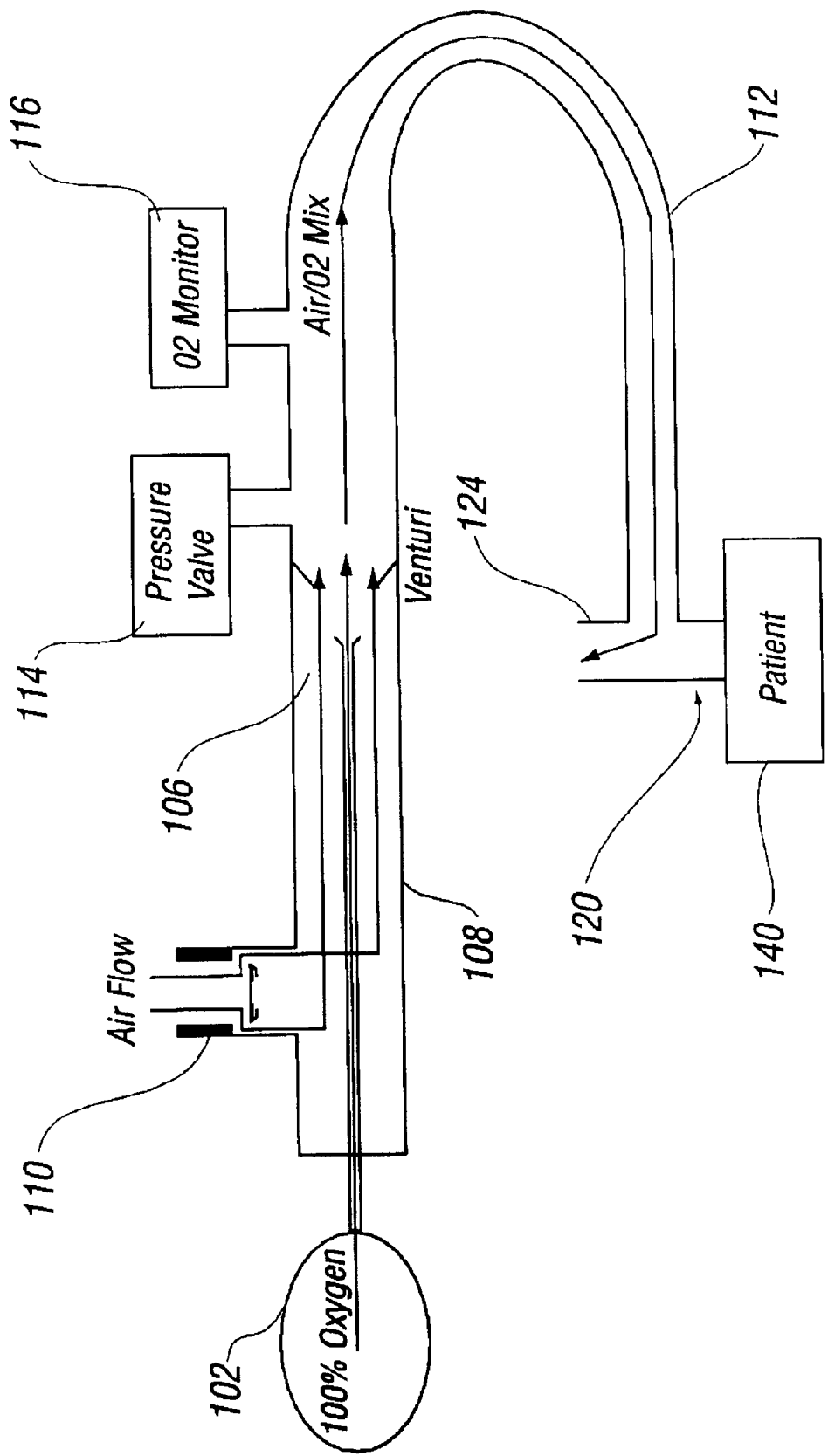

Referring now to FIGS. 4, 5, and 6, the operation of the apparatus is now described. In the state where the aperture 124 is open, air is entrained into conduit 108 through the valve 110 and ultimately mixes with the pure oxygen passing through the venturi. Pressure release valve 114 is closed and an air/oxygen mixture ultimately exhausts to atmosphere through the outlet 124 of the T-occluder 120. In these figures, the mask portion of the T-occluder is placed against the mouth of the living being or patient which is represented at 140, and this ensures that the air/oxygen mixture is exhausted through outlet 124 as opposed to being forced into the lungs of patient 140 as shown by the arrow 142.

Once the outlet 124 is blocked by an operator as shown at 144, the pressure within both first conduit 108 and second conduit 112 automatically increases, the pressure valve 110 closes, and air is no longer entrained therethrough by virtue of the flow of oxygen through venturi 106. In this condition, the volume of oxygen/air mixture is forced through conduit 112 and into the lungs of the patient 140 as shown by arrow 146. It will be appreciated that as the pressurized oxygen emerging into the apparatus through venturi 106 forces the oxygen/air mixture into the patient, this mixture will be progressively be replaced by substantially pure oxygen, and once the lungs of the patient 140 have been inflated to the required degree, the pressure within the conduit 112 will increase above a threshold pressure level of the pressure release valve 114. Once this condition is achieved, the pure oxygen will merely exhaust through the valve 114, and the patient will not receive any of the substantially pure oxygen. The threshold pressure of valve 114 can be adjusted as desired by the operator.

Thereafter, the operator uncovers outlet 124 as shown in FIG. 6, the exhaled gases of the patient pass directly through said outlet, the pressure within conduits 108 and 112 is immediately reduced which allows the valve 110 to open and air to once again be entrained by the flow of oxygen through the venturi. The mixed oxygen/air stream then displaces the substantially pure oxygen from conduit 112 until only the gas mixture is present within conduit 112, whereafter the operator can repeat the process described. The oxygen monitor 116 enables the operator to air determine when the outlet can again be blocked so that a mixture of oxygen/air of the required oxygen concentration can be delivered to the patient. Of course the oxygen monitor may be disposed at any desired position along conduit 112.

It is also to be mentioned that the aperture through the pressure valve 110 may be adjusted when the valve is open so that the quantity of air entrained during operation of the apparatus can be adjusted. In this manner the oxygen concentration in the resulting mixed oxygen/air gas stream can be altered as required by the operator.

What is claimed is:

1. A device suitable for aiding, forcing or initiating the breathing of living beings, said device comprising a venturi device within a first conduit by which air can be entrained through said first conduit from behind said venturi device, a second conduit of predetermined length provided in front of said venturi device, said second conduit being of a significantly greater diameter than a throat of the venturi device so as not to adversely affect the entrainment of air thereby, said second conduit being coupled to a mask having first and second apertures through which gas can exhaust, said first aperture being disposed in sealing relationship with an air intake passage of a living being, and further comprising a pressure actuable valve having open and closed conditions, said pressure actuable valve being positioned in the first conduit upstream of said venturi with entrained air necessarily passing through said pressure actuable valve when open, said pressure actuable valve being automatically closed when the second aperture of the mask is blocked thus immediately increasing the pressure in the first and second conduit and constraining a volume of gas within the second conduit to be delivered under pressure to the living being through the first aperture of said mask.

2. A device according to claim 1 wherein a pressure release valve is provided downstream of said venturi device in said second conduit to allow venting of gas therethrough when the pressure within said second conduit exceeds a predetermined threshold.

3. A device according to claim 2 wherein the pressure release valve is adjustable so that a threshold pressure can be set as desired.

4. A device according to claim 1 wherein said device is coupled to a source of substantially pure oxygen.

5. A device according to claim 1 wherein the length of the second conduit and a threshold pressure of the pressure value are determined according to the capacity of the lungs of the living being.

6. A device according to claim 1 wherein the pressure actuable valve is adjustable so that the volumetric quantity of entrained air, and thus a predetermined concentration of oxygen within the second conduit can be selectively altered when the second aperture of the mask is open and air is being entrained.

7. A device according to claim 1 wherein the venturi is adjustable so that the amount of ambient air entrained can be adjusted.

8. A device according to claim 1 wherein the second aperture in the mask is of a suitable size to allow an operator of the device to cover and uncover said second aperture with a finger.

* * * * *